United States Patent [19]
Pei et al.

[11] Patent Number: 5,208,343

[45] Date of Patent: May 4, 1993

[54] TETRAHYDROPYRIDINE OXIME COMPOUNDS

[75] Inventors: Yazhong Pei, Ann Arbor; Haile Tecle, Ypsilanti, both of Mich.

[73] Assignee: Warner-Lambert Company, Morris Plains, N.J.

[21] Appl. No.: 856,233

[22] Filed: Mar. 24, 1992

[51] Int. Cl.$^5$ .................... C07D 213/04; A61K 31/44
[52] U.S. Cl. ........................................ 546/284; 546/338
[58] Field of Search ................................ 546/284, 338

[56] References Cited

U.S. PATENT DOCUMENTS

| | | | |
|---|---|---|---|
| 3,004,979 | 10/1961 | Druey | 546/338 |
| 4,798,841 | 1/1989 | Downs et al. | 546/338 |
| 4,929,734 | 5/1990 | Coughenour et al. | 546/338 |

OTHER PUBLICATIONS

*Trends in Neuroscience*, 10(11):444–446 (1987), Quirion et al., "Classification and Nomenclature of Phencyclidine . . . ".

*Clinical Neuropharmacology*, 11(2):105–119, S. Deutsch et al., "The Sigma Receptor: A Novel Site Implicated . . . ".

*Molecular Pharmacology*, 32:772–784, (1987), B. Largent et al. "Structural Determinants of σ Receptor Affinity".

*Pharmacological Reviews*, 42(4):355–402, (1990), J. Walker, et al., "Sigma Receptors: Biology and Funtion".

*Drug Development Research*, 11:65–70 (1987), D. Taylor et al., "Potential Antipsychotic BMY 14802 Selectively . . . ".

*Clinical Neuropharmacology*, 11(6):565, (1988), K. Jansen, "The Sigma Receptor and Movement Disorders".

*Neurology*, 38:961–965 (1988), J. Walker et al., "Evidence for a Role of Haloperidol-Sensitive σ-'Opiate'. . . ".

*European J. of Pharmacology*, 147:153–154 (1988), W. Bowen et al., "Altered Haloperidol-Sensitive σ Receptors . . . ".

*Science*, 240:219–221 (1988), T. Su et al., "Steroid Binding at σ Receptors Suggest a Link Between . . . ".

*European J. of Pharmacology*, 148:467–470 (1988), T. Su et al., "Correlation of Inhibitory Potencies of Putative . . . ".

*Soc. for Neuroscience Abstracts*, 13(2):1437 (1987), S. Wolfe et al., "Sigma Receptors in Human Peripheral . . . ".

*J. Parmacology and Experimental Therapeutics*, 197(3):517–532, W. Martin et al., "The Effects of Morphine . . . ".

*Society for Neuroscience Abstracts*, 17:333 (1991), L. Cook et al., "The Pharmacology of a Sigma . . . ".

*Primary Examiner*—C. Warren Ivy
*Assistant Examiner*—Zinna N. Davis
*Attorney, Agent, or Firm*—Ruth H. Newtson; Michael J. Atkins

[57] ABSTRACT

Pharmaceutically useful compounds in the treatment of depression, psychoses, and inflammatory diseases having the following structure:

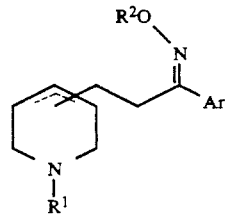

4 Claims, No Drawings

TETRAHYDROPYRIDINE OXIME COMPOUNDS

FIELD OF INVENTION

The present invention relates to novel compounds which have affinity for the sigma binding site, rendering said compounds useful in treating conditions of the central nervous system including depression, anxiety, psychoses, dystonias, epilepsy, stroke as well as diseases of the immune system including inflammatory diseases.

BACKGROUND OF THE INVENTION

The classification and nomenclature of phencyclidine and sigma receptor sites have been reviewed (Trends Neuroscience 1987; 10:444 446 and Clin. Neuropharmacol. 1988; 11:105). The structural determinants of sigma receptor affinity have been described (Mol. Pharmacol. 1987; 32:772 784). The compounds of the present invention have been found to have high affinity for the sigma site.

Sigma binding sites are found in the brain (J. M. Walker, et al, Pharmacol. Rev. 1990; 42:355) and have been implicated in a number of disease states such as psychosis and various motor disorders (dystonias and dyskinesia). For example, the mode of action of the potential antipsychotic rimcazole and BMY 14802 is believed to be related in part to an interaction through sigma sites (D. P. Taylor, et al, Drug Dev. Res. 1987; 11:65). However, controversy exists as to the actual role of sigma sites in antipsychotic drug action (K. L. R. Jansen, Clin. Neuropharm. 1988; 11:565). High concentrations of sigma receptors are found in the red nucleus (RN), an area involved in posture and movement. It is reported that microinjection of sigma ligands to the RN of rats causes abnormal postural changes (dystonias) (J. M. Walker, et al, Neurology 1988; 38:961). Abnormal sigma binding patterns have been observed in brain from genetically dystonic rats (W. D. Bowen, et al, Eur. J. Pharmacol. 1988; 147:153). Also, certain steroids are naturally occurring ligands for the sigma binding site (T. Su, et al, Science 1988; 240:219), which raises the possibility that the sigma site may mediate some aspects of steroid-induced mental disturbances and alterations in immune functions. Further, sigma binding sites are found in spleen and lymphocytes (T. Su, et al, Eur. J. Pharmacol. 1988; 148:467 and S. A. Wolfe, et al, Soc. Neurosci. Abstr. 1987; 13:1437), suggesting that sigma binding sites may play an important role in the immune system.

Since the sigma binding site was first postulated in 1976 (W. R. Martin, et al, J. Pharmacol. Exp. Ther. 1976; 197:517), a great number of studies have been carried out to discover its nature and function (J. M. Walker, Pharmacol. Rev. 1990; 42:355). Despite the considerable amount of work, there are no known commercially available agonists or antagonists for the sigma binding sites. DuP 734, [1-(cyclopropylmethyl)-4-(2',4"-fluoroethyl) 2'-oxoethyl)piperidine HBr] which has antipsychotic properties, is believed to be a sigma binding site antagonist (L. Cook, et al, Abstract 133.8, p. 333, Society for Neuroscience, 21st Annual Meeting, New Orleans, La., November 10-15, 1991). The availability of selective sigma ligands is highly desirable as tools to further unravel the biological and pharmacological role played by sigma sites.

SUMMARY OF THE INVENTION

The present invention provides novel pharmaceutically useful tetrahydropyridine compounds having the following general formula:

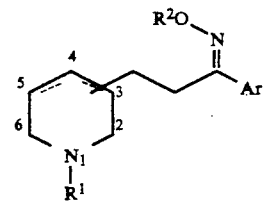

Formula I wherein the dotted line indicates a bond between either the carbons at the 3- and 4-positions or the 4- and 5-positions;
wherein the side chain

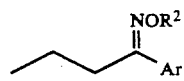

is attached to either the 3- or 4-position of the tetrahydropyridine ring;
wherein $R^1$ is hydrogen; a straight or branched alkyl group having from 1 to 6 carbon atoms; a cycloalkylmethyl group wherein the cycloalkyl moiety has from 3 to 6 carbon atoms; phenyl$(CH_2)_n$ wherein n is one or two and wherein the phenyl ring is unsubstituted or is substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro, or $-NR_3R_4$ wherein each of $R_3$ and $R_4$ is individually hydrogen or a straight or branched alkyl having from 1 to 4 carbon atoms;
wherein Ar is 2- or 3-thienyl, phenyl, or phenyl substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro, or $-NR_3R_4$ wherein each of $R_3$ and $R_4$ has the meaning defined above;
wherein $R_2$ is hydrogen, a straight or branched alkyl having from 1 to 6 carbon atoms, benzyl, or phenethyl; and pharmaceutically acceptable salts thereof.

The individual geometric isomers and optical isomers of the compounds of general Formula I are also included within the scope of the present invention.

Compositions containing compounds of Formula I are also included within the scope of the present invention as are novel methods of using the compounds and compositions. In particular, the present invention provides a method of treating depression in a mammal in need of such treatment comprising the administration of an antidepressant effective amount of a compound of Formula I above in combination with a pharmaceutically acceptable carrier.

The present invention also provides a method of treating psychoses, e.g., schizophrenia, in a mammal in need of such treatment comprising the administration of an antipsychotic effective amount of a compound of Formula I above in combination with a pharmaceutically acceptable carrier.

Additionally, the present invention provides a method of treating inflammation in a mammal in need of such treatment comprising the administration of an antiinflammatory effective amount of a compound of Formula I above in combination with a pharmaceutically acceptable carrier.

The present invention also provides novel pharmaceutical compositions useful in treating the conditions enumerated above.

DETAILED DESCRIPTION OF INVENTION acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane- and ethanesulfonic, hydroxymethane-, and hydroxyethanesulfonic, and the like (see, for example, "Pharmaceutical Salts", J. Pharm. Sci. 1977; 66(1):1–19).

The compounds of the present invention as represented by general Formula I are prepared as outlined in the general reaction scheme set forth below wherein the various substituents Ar, $R^1$, and $R^2$ have the meanings defined in Formula I and X is halogen, for example, chlorine or bromine.

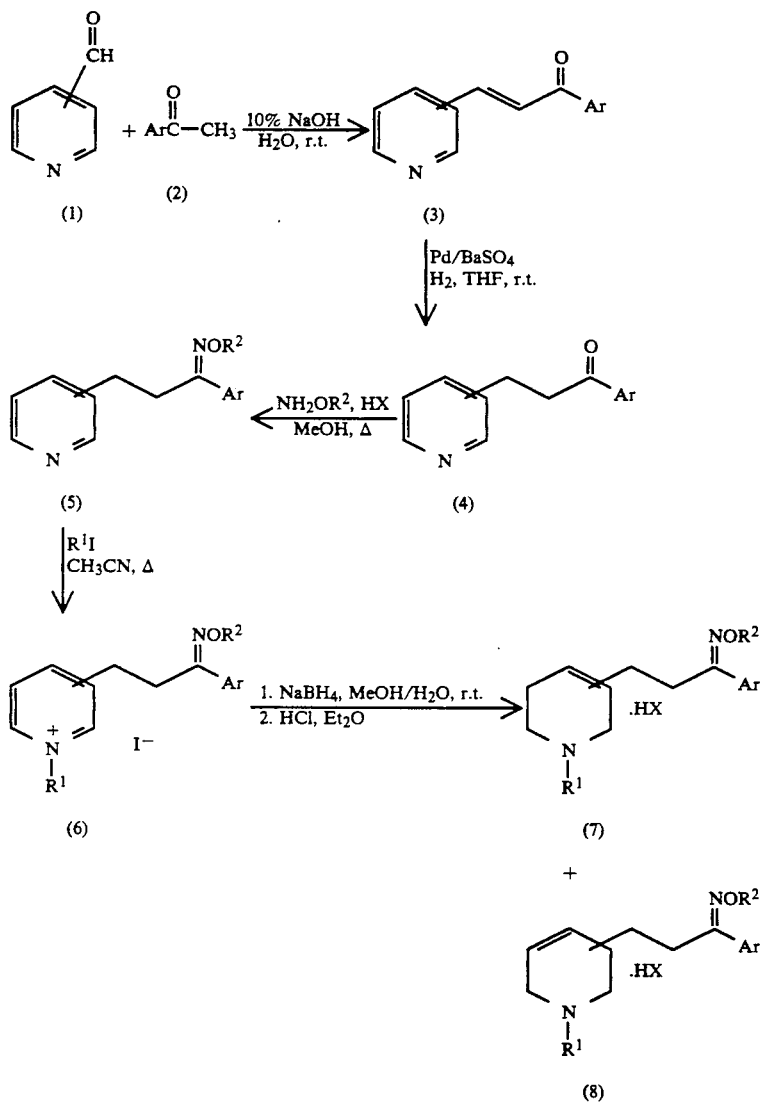

In the above general Formula I illustrative examples of straight or branched alkoxy groups having from 1 to 4 carbon atoms are methoxy, ethoxy, n-propoxy, isopropoxy, and n butoxy. Illustrative examples of straight or branched alkyl groups having from 1 to 4 carbon atoms are methyl, ethyl, n-propyl, isopropyl, and n-butyl.

By virtue of the basic nitrogen atom in the tetrahydropyridine ring, the compounds of the present invention form pharmaceutically acceptable acid addition salts with organic and inorganic acids. Examples of suitable acids for the formation of pharmaceutically The pyridine carboxaldehyde (1) and aryl ketone (2) are reacted in water in the presence of sodium hydroxide at room temperature to give the 1-aryl-3-(3-pyridinyl)-2-propene-1-one (3) which is hydrogenated in a Parr hydrogenation apparatus using, for example, 10% palladium on barium sulfate to give the pyridinylpropanone (4). The pyridinylpropanone (4) is reacted with an appropriate hydroxylamine of the formula $NH_2OR_2 \cdot HX$ wherein $R_2$ and X have the meanings defined above to give the oxime (5), which is alkylated in, e.g., acetonitrile with a reagent of the formula R¹X wherein R¹ and X have the meanings given above to give the quaternary salt (6). The iodate is reduced with a metal hydride such as sodium borotetrahydride to give the products (7) and (8).

The following specific examples further illustrate the synthesis of compounds of the present invention.

EXAMPLE 1

1
Phenyl-3-(1,2,3,6-tetrahydro-1-propyl-3-pyridinyl)-1-propanone oxime oxalate and
1-phenyl-3-(1,2,5,6-tetrahydro-1-propyl-3-pyridinyl)-1-propanone oxime oxalate (a) 3 (3-Pyridinyl) 1-phenyl 2 propen-1-one To a suspension of 3 pyridinecarboxaldehyde (18.9 mL, 0.20 mol) and acetophenone (23.4 mL, 0.20 mol) in 200 mL water at room temperature with vigorous stirring was added dropwise 5% aqueous sodium hydroxide (200 mL) over a 45-minute period. The reaction mixture was stirred for 12 hours. White solid was formed during the reaction. Dichloromethane (500 mL) was added to dissolve the solid. The organic layer was separated, washed with water (300 mL×3), and dried over anhydrous sodium sulfate. After the drying agent and solvent were removed, the crude product was recrystallized to give the title compound as yellow solid (35.62 g, 85%), mp 113°–114° C.

(b) 3-(3-Pyridinyl)-1-phenylpropan-1-one

To a solution of 3 (3-pyridinyl)-1 phenyl-2-propen-1-one (24.8 g, 0.12 mol) in 400 mL tetrahydrofuran was added 10% Pd/BaSO₄ (2 g). The slurry was hydrogenated at room temperature on a Parr hydrogenation apparatus. The reaction was monitored by pressure drop. The hydrogenation was complete after 40 minutes. After the catalyst was filtered off on celite, the solvent was removed under vacuum to give a dark brown oil. The crude product was purified on flash silica gel column using a gradient eluent system ($CH_2Cl_2 \rightarrow MeOH-CH_2Cl_2$, 3:97) to furnish the title compound as a pale yellow solid (22.54 g, 91%), mp 86°–87° C.

(c) 3-(3-Pyridinyl)-1-phenylpropan-1-oxime 3-(3-Pyridinyl)-1 phenylpropan 1-one (6.34 g, 0.03 mol) and hydroxylamine hydrochloride (4.17 g, 0.06 mol) was dissolved in methanol (100 mL). The mixture was refluxed for 12 hours. The solvent was removed under vacuum. The residue was stirred in a mixture of dichloromethane (150 mL) and 10% aqueous sodium carbonate (150 mL). The aqueous layer was separated and extracted with dichloromethane (200 mL ×3). The combined organic layer was dried over anhydrous sodium sulfate. After the drying agent and solvent were removed, the crude product was purified on a silica gel column using a gradient eluent system ($CH_2Cl_2 \rightarrow MeOH-CH_2Cl_2$, 5:95) to afford the title compound as a white solid (5.97 g, 87.9%), mp 107°–108° C.

(d)
3-[3-(Hydroxyimino)-3-phenylpropyl]-1-propyl-pyridinium iodide

To a solution of 3-(3-pyridinyl)-1-phenylpropan-1-one oxime (4.79 g, 0.021 mol) in acetonitrile (50 mL) was added 1-iodopropane (3.10 mL, 0.032 mol). The mixture was then refluxed for 12 hours. Solvent was removed to dryness under vacuum to give a dark brown oil (8.46 g, 100%). The crude product was used in the next step without further purification.

(e)
1-Phenyl-3-(1,2,3,6-tetrahydro-1-propyl-3-pyridinyl)-1-propanone oxime oxalate and
1-phenyl-3-1,2,5,6-tetrahydro-1-propyl-3-pyridinyl)-1-propanone oxime oxalate To a 100-mL round-bottom flask containing mixed solvent of methanol and water (1:1, 150 mL) at 0° C. was added powdered sodium borohydride (1.59 g, 0.042 mol) followed immediately by addition of a solution of 3-[3-(hydroxyimino)-3-phenylpropyl]-1-propyl-pyridinium iodide (8.46 g, 0.021 mol) in methanol (200 mL). The mixture was stirred for an additional 3 hours and allowed to warm to room temperature. Solvent was removed to dryness under vacuum. The residue was dissolved in dichloromethane (200 mL) and water (200 mL). The aqueous layer was separated and extracted with dichloromethane (150 mL×3). The combined organic layer was dried (sodium sulfate) and the solvent removed to give a mixture of the title compounds as brown oil. The compounds were separated (silica gel column) and converted to their respective oxalic salts. The salts were recrystallized from isopropanol to give
(a) 1 Phenyl-3-(1,2,3,6-tetrahydro-1-propyl-3-pyridinyl)-1-propanone oxime oxalate; white solid, 3.27 g, mp 212°–213° C., and
(b) 1-Phenyl-3-(1,2,5,6-tetrahydro-1-propyl-3-pyridinyl)-1-propanone oxime oxalate; white solid, 1.42 g, mp 201°–205° C.

EXAMPLE 2

1-(4-Methoxyphenyl)-3-(1,2,3,6-tetrahydro-1-propyl-3-pyridinyl)-1-propanone oxime oxalate and
1-(4-Methoxyphenyl)-3-(1,2,5,6-tetrahydro-1-propyl-3-pyridinyl)-1-propanone oxime oxalate (a)
3-(3-Pyridinyl)-1-(4-methoxyphenyl)-2-propen-1-one When in the procedure of Example 1(a) an appropriate amount of p-methoxyacetophenone was substituted for acetophenone, the above 2(a) compound was obtained. Yield: 65.7%, mp 113°–114° C.

(b) 3-(3-Pyridinyl)-1-(4-methoxyphenyl)propan-1-one

When in the procedure of Example 1(b) an appropriate amount of Compound 2(a) was substituted for 3-(3-pyridinyl)-1-phenyl-2-propen-1-one, the above 2(b) compound was obtained. Yield: 92%, mp 76°–78° C.

(c) 3-(3-Pyridinyl)-1-(4-methoxyphenyl)propan-1-one oxime

When in the procedure of Example 1(c) an appropriate amount of the 2(b) compound was substituted for 3-(3-pyridinyl)-1-phenylpropan-1-one, the above compound 2(c) was obtained. Yield: 96.1%, white crystal, mp 101°–102° C.

(d)
3-[3-(Hydroxyimino)3-(4-methoxyphenyl)propyl]-1-propylpyridinium iodide

When in the procedure of Example 1(d) an appropriate amount of Compound 2(c) was substituted for 3-(3-pyridinyl)-1-phenylpropan-1-one oxime, the above 2(d)

compound was obtained as an oil and was used in the next step without further purification.

(e) 1-(Methoxyphenyl-3-(1,2,3,6-tetrahydro-1-propyl-3-pyridinyl)-1-propanone oxime oxalate and 1-(4-Methoxyphenyl)-3-(1,2,5,6-tetrahydro-1-propyl-3-pyridinyl)-1-propanone oxime oxalate When in the procedure of Example 1(e) an appropriate amount of Compound 2(d) was substituted for 3-[3-(1-propylpyridiniumyl)]-1-phenylpropan-1-one oxime iodate, the title compound was obtained.

(a) 1-(4-Methoxyphenyl) 3-(1,2,3,6-tetrahydro-1-propyl-3-pyridinyl)-1-propanone oxime oxalate; white solid (1.48 g), mp 175°–177° C.

(b) 1-(4-Methoxyphenyl-3-(1,2,5,6-tetrahydro-1-propyl-3-pyridinyl)-1-propanone oxime oxalate; white solid (2.57 g), mp 173°–176° C.

The utility of the compounds of the present invention is demonstrated by various in vitro studies. Sigma binding affinities are measured using [$^3$H]-(+)-3-(3'-hydroxyphenyl) N (1'-propyl)piperidine, referred to in the following Table I as 3PPP. This test is carried out according to the procedures of B. L. Largent, et al, Proc. Natl. Acad. Sci., USA, 1984; 81:5618. The affinity of the compounds of the present invention for dopamine receptors was determined in vitro with the dopamine antagonist [$^3$H]spiperone according to the procedure of S. Urwyler, et al, J. Neurochem. 1986; 46:1058. The ability of the compounds to bind muscarinic antagonist sites was determined in vitro using [$^3$H]-quinuclidinyl benzylate (RQNB) according to the procedure of M. Watson, et al, J. Pharmacol. Exp. Ther. 1986; 237:411. The test results are set forth below:

TABLE I

| Example Number | [$^3$H]3PPP IC$_{50}$ nM | RQNB % Inhib at $10^{-6}$ M | RBSP IC$_{50}$ nM |
| --- | --- | --- | --- |
| 1(e)(a) | 2.07 | 27% | >1000 |
| 1(e)(b) | 1.99 | 10% | >1000 |
| 2(e)(a) | 6.49 | 6% | >1000 |
| 2(e)(b) | 2.39 | 9% | >1000 |

In therapeutic use as agents for treating depression, psychoses, or inflammation, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

We claim:

1. A compound of the formula

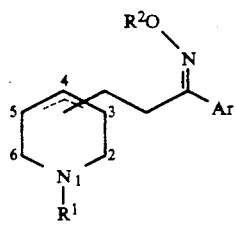

wherein the dotted line indicates a bond between either the carbons at the 3- and 4-positions or the 4- and 5-positions;
wherein the side chain

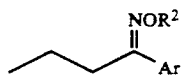

is attached to either the 3- or 4-position of the tetrahydropyridine ring;
wherein $R^1$ is hydrogen; a straight or branched alkyl group having from 1 to 6 carbon atoms; a cycloalkylmethyl group wherein the cycloalkyl moiety has from 3 to 6 carbon atoms; phenyl$(CH_2)_n$ wherein n is one or two and wherein the phenyl ring is unsubstituted or is substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro, or —$NR_3R_4$ wherein each of $R_3$ and $R_4$ is individually hydrogen or a straight or branched alkyl having from 1 to 4 carbon atoms;
wherein Ar is 2- or 3-thienyl, phenyl, or phenyl substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro, or —$NR_3R_4$ wherein each of $R_3$ and $R_4$ has the meaning defined above;
wherein $R_2$ hydrogen, a straight or branched alkyl having from 1 to 6 carbon atoms, benzyl, or phenethyl; a pharmaceutically acceptable salt thereof or a geometric and optical isomer thereof.

2. A compound of claim 1 wherein Ar is phenyl or substituted phenyl.

3. A compound of claim 1 wherein the side chain

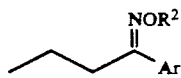

is attached to the 3-position of the tetrahydropyridine ring.

4. A compound of claim 1 which is
1-phenyl-3-(1,2,3,6-tetrahydro-1-propyl-3-pyridinyl) 1-propanone oxime oxalate;
1-phenyl-3-(1,2,5,6 tetrahydro-1-propyl-3-pyridinyl)-1-propanone oxime oxalate;
1-(4-methoxyphenyl)-3-(1,2,3,6-tetrahydro-1-propyl-3-pyridinyl)-1-propanone oxime oxalate; or
1-(4-methoxyphenyl)-3-(1,2,5,6-tetrahydro-1-propyl-3-pyridinyl)-1-propanone oxime oxalate.

* * * * *

UNITED STATES PATENT AND TRADEMARK OFFICE
CERTIFICATE OF CORRECTION

Patent No:    5,208,343
Dated:        May 4, 1993
Inventor(s):  Pei et al.

It is certified that error appears in the above-identified patent and that said Letters Patent is hereby corrected as shown below:

Column 10, line 11, replace the phrase "$R_2$ hydrogen" with the phrase --$R_2$ is hydrogen--.

Column 10, line 14, replace the phrase "and optical" with the phrase --or optical--.

Signed and Sealed this

Twenty-ninth Day of March, 1994

Attest:

BRUCE LEHMAN

*Attesting Officer*   Commissioner of Patents and Trademarks